United States Patent [19]

Huss, Jr. et al.

[11] Patent Number: 4,935,577

[45] Date of Patent: Jun. 19, 1990

[54] HYDROCARBON PROCESSES COMPRISED OF CATALYTIC DISTILLATION USING LEWIS ACID PROMOTED INORGANIC OXIDE CATALYST SYSTEMS

[75] Inventors: Albin Huss, Jr., Chadds Ford; Clinton R. Kennedy, West Chester, both of Pa.

[73] Assignee: Mobil Oil Corp., New York, N.Y.

[21] Appl. No.: 297,805

[22] Filed: Jan. 17, 1989

Related U.S. Application Data

[63] Continuation-in-part of Ser. No. 219,129, Jul. 15, 1988.

[51] Int. Cl.$^5$ .............................................. C07C 2/58
[52] U.S. Cl. .................................... 585/726; 585/728
[58] Field of Search .............................. 585/726, 728

[56] References Cited

U.S. PATENT DOCUMENTS

| | | | |
|---|---|---|---|
| 2,345,095 | 3/1944 | Brumer et al. ....................... | 585/726 |
| 2,450,764 | 10/1948 | Meyers ................................. | 208/134 |
| 3,293,192 | 12/1966 | Maher et al. ........................ | 252/430 |
| 3,855,342 | 12/1974 | Huang et al. .................... | 260/683.44 |
| 3,862,258 | 1/1975 | Huang et al. .................... | 260/683.44 |
| 4,016,218 | 4/1977 | Haag et al. ....................... | 260/671 R |
| 4,215,011 | 7/1980 | Smith, Jr. .............................. | 252/426 |
| 4,232,177 | 11/1980 | Smith, Jr. . | |
| 4,242,530 | 12/1980 | Smith, Jr. ............................ | 585/800 |
| 4,307,254 | 12/1981 | Smith, Jr. ............................ | 568/697 |
| 4,308,414 | 12/1981 | Madgavkar et al. ................ | 585/525 |
| 4,325,994 | 4/1982 | Kitashima et al. ................. | 427/37.8 |
| 4,374,296 | 2/1983 | Haag et al. ......................... | 585/739 |
| 4,384,161 | 5/1983 | Huang . | |
| 4,418,235 | 11/1983 | Haag et al. ......................... | 585/407 |
| 4,440,871 | 4/1984 | Lok et al. ........................... | 502/214 |
| 4,503,023 | 3/1985 | Breck et al. ........................ | 423/328 |
| 4,510,336 | 4/1985 | Hearn ................................... | 568/697 |
| 4,520,221 | 5/1985 | Hsia Chen .......................... | 585/517 |
| 4,554,143 | 11/1985 | Messina et al. .................... | 423/306 |
| 4,567,029 | 1/1986 | Wilson et al. ...................... | 423/306 |
| 4,666,875 | 5/1987 | Pellet et al. ......................... | 502/65 |
| 4,742,033 | 5/1988 | Harris et al. ........................ | 502/68 |

FOREIGN PATENT DOCUMENTS

0189683 12/1985 European Pat. Off. .

OTHER PUBLICATIONS

Catalytic Distillation, Chemical Processing (Feb., 1987), W. Stadig.
J. Shoemaker et al., Cumene by Catalytic Distillation, Hydrocarbon Processing, pp. 57 & 58 (Jun., 1987).
Friedel-Crafts and Related Reactions, Interscience Publishers, (1963), vol. I, pp. 189-191 & 214-291.
J. Catalysis, 6, pp. 278-287 (1966)-Catalysis by Crystalline Aluminosilicates.
J. Catalysis, 61, pp. 390-396 (1980), Chemical and Physical Properties of ZSM-5 Substitutional Series, D. H. Olson, W. O. Haag and R. M. Lago.
Fixed-Bed Catalytic Process to Produce Synthetic Lubricants from Decene-1, Industrial Engineering Product Research Development, vol. 22, No. 4, pp. 675-670.

*Primary Examiner*—Curtis R. Davis
*Attorney, Agent, or Firm*—Alexander J. McKillop; Charles J. Speciale; Robert B. Furr, Jr.

[57] ABSTRACT

This invention relates to catalytic distillation utilizing Lewis acid promoted non-zeolitic inorganic oxide, large pore crystalline molecular sieve and/or ion exchange resin systems. Alkylation and oligomerization processes are adapted to this catalytic distillation technique.

26 Claims, 1 Drawing Sheet

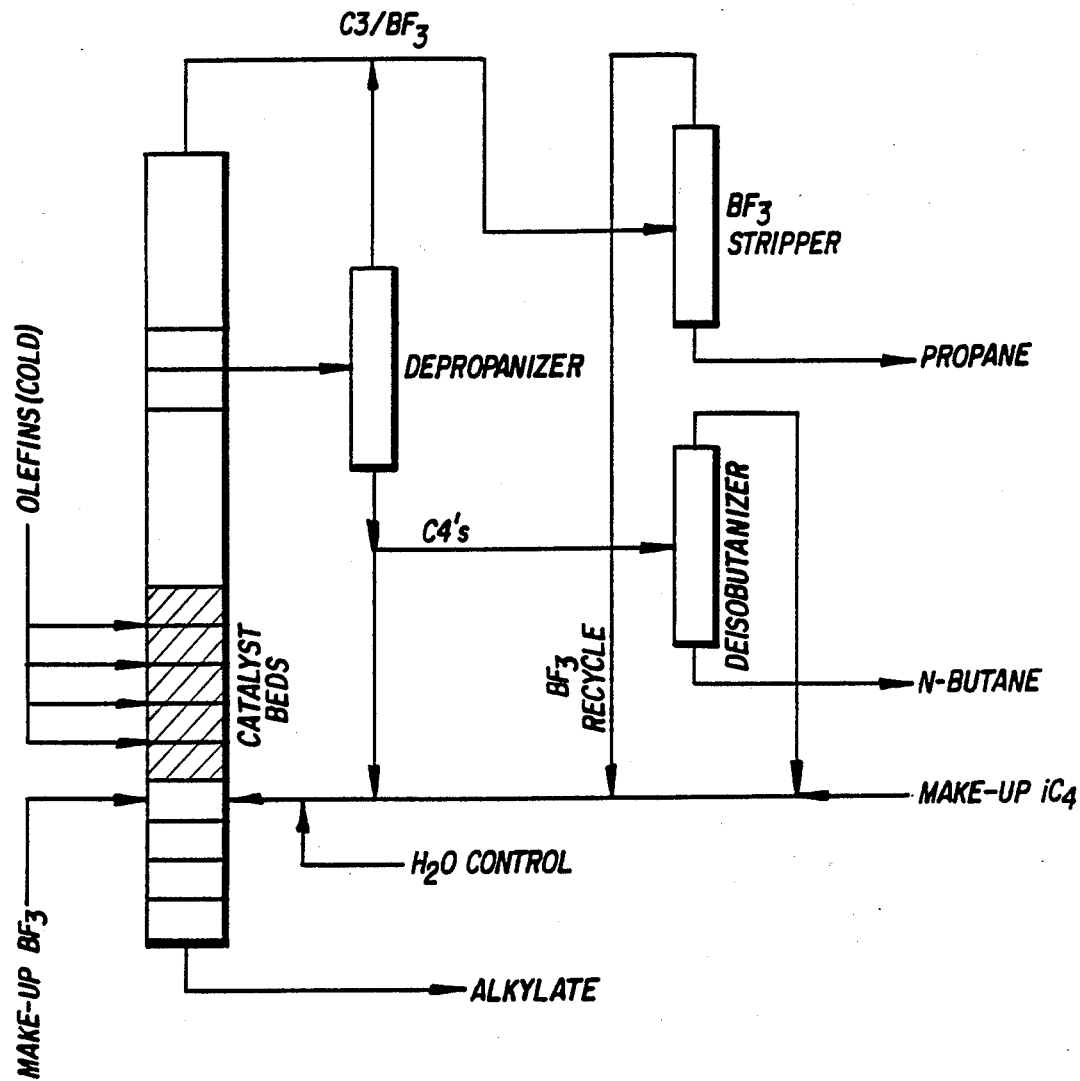

HYDROCARBON PROCESSES COMPRISED OF CATALYTIC DISTILLATION USING LEWIS ACID PROMOTED INORGANIC OXIDE CATALYST SYSTEMS

This application is a continuation-in-part of application Ser. No. 219,129, filed July 15, 1988, 1988 entitled "Heterogeneous Isoparaffin/Olefin Alkylation". The applications are commonly assigned. The above application is hereby incorporated by reference.

FIELD OF THE INVENTION

The present invention is directed to catalytic distillation using a catalyst consisting essentially of a Lewis acid promoted inorganic oxide. Specific hydrocarbon processes utilized are alkylation and oligomerization.

BACKGROUND OF THE INVENTION

This invention relates to combining chemical reaction with product separation, that is, catalytic distillation. Continuous removal of reaction products is a unique feature that gives catalytic distillation its technical and economic advantages. Advantages include lower energy requirements, higher yields, good product purity, and lower capital investment.

In catalytic distillation, a reaction zone, containing catalysts, is fitted into a fractionation tower conventionally equipped with an overhead condenser, reflux pump, reboiler, and control instrumentation. Depending upon boiling points, feed components are introduced above or below the catalyst bed. Products are continuously removed from the reaction zone by the distillation process.

Catalytic distillation is suitable only for chemical reactions where the distillation of reaction components occurs in the same temperature range as the reaction. Thus, operation above the critical point can be a limitation, and the presence of azeotropes or close boiling components may cause difficulties.

The catalyst must be stable and insoluble in the feed or product. It should be relatively immune to poisoning because frequent replacement can be costly. The selective catalyst, which must be a solid material, can be contained in pockets stitched into fiberglass cloth. The cloth is rolled into bundles with alternate layers of wire mesh. In operation, liquid flows freely into and out of the bundles, providing a constant exchange over the catalyst surface.

Multiple bundles of various diameters are used to cover the cross section of the distillation column and each layer of bundles is staggered to prevent by-passing. The total bed height, or reaction zone, and its position in the column are determined by the feed type and composition, and the products and purity desired.

The reaction occurs in the liquid phase in the presence of a solid catalyst.

Catalytic distillation has been used commercially to produce methyl tert-butyl ether. See W. Stadig, *Catalytic Distillation*, Chemical Processing (February, 1987). See U.S. Pat. Nos. 4,232,177 and 4,307,254.

Catalytic distillation has also been used to produce cumene by alkylating propylene with benzene. See J. Shoemaker et al, *Cumening By Catalytic Distillation*, Hydrocarbon Processing, p. 57 (June, 1987).

U.S. Pat. Nos. 4,242,530 and 4,215,011 relate to a catalytic distillation technique for the separation of isobutene from a mixture comprising n-butene and isobutene. Catalyst suitable for the process are taught to be cation exchangers, which contain sulfonic acid groups, and which has been obtained by polymerization or copolymerization of aromatic vinyl compounds followed by sulfonation.

U.S. Pat. No. 4,510,336 relates to transetherification carried out in a catalytic distillation reactor. There, an ether is fed to a catalyst bed to partially dissociate it into a first olefin and a first alcohol while concurrently feeding a second olefin or a second alcohol having a higher boiling point to form a second ether. Catalyst suitable for the distillation are cation exchangers which contain sulphonic acid groups.

European Patent Application No. 189,683 relates to aromatic compounds that are alkylated in a catalytic distillation. The catalyst can be a suitable cation exchange resin including those containing sulphonic acid groups. The catalyst can also be a molecular sieve, which includes both naturally occurring zeolites and synthetic zeolites.

U.S. Pat. No. 4,384,161 relates to a heterogeneous isoparaffin/olefin alkylation. This process comprises contacting the isoparaffins and olefins with a composite catalyst comprising a large pore zeolite and a Lewis acid. Similary, U.S. Pat. Nos. 3,855,342 and 3,862,258 relate to such alkylations but using a complex of a macroreticular acid cation exchange resin and $BF_3$ with or without the addition of water. None of these processes relate to catalytic distillation.

The preceding references are incorporated by reference.

The present invention relates to alkylation and oligomerization processes utilizing a catalyst comprising a Lewis acid promoted non-zeolitic solid inorganic oxide, large pore crystalline molecular sieve and/or ion exchange resin, which can be in the presence of water, which is effected by catalytic distillation techniques.

SUMMARY OF THE INVENTION

This invention relates to an alkylation process comprising:

(a) feeding (1) an isoparaffin containing from 4 to 20 carbon atoms and (2) an olefin containing from 2 to 12 carbon atoms to a distillation column reactor into a feed zone, (b) concurrently in the distillation column reactor:

contacting the isoparaffin and olefin with a composite catalyst consisting essentially of a Lewis acid and a non-zeolitic solid inorganic oxide, in a distillation reaction zone thereby catalytically reacting the isoparaffin with the olefin to form alkylate, (c) withdrawing the alkylate from the distillation column reactor below the feed zone, and (d) withdrawing isobutane from the distillation column reactor above the feed zone.

This invention also relates to an oligomerization process comprising:

(a) feeding alpha-olefins having from 3 to 12 carbon atoms to a distillation column reactor into a feed zone, (b) concurrently in the distillation column reactor:

contacting the alpha-olefins with a composite catalyst consisting essentially of a Lewis acid with a non-zeolitic solid inorganic oxide, in a distillation reaction zone thereby catalytically reacting the alpha-olefins to form oligomer, (c) withdrawing the oligomer from the distillation column reactor below the feed zone, and (d) withdrawing alpha-olefins from the distillation column reactor above the feed zone.

BRIEF DESCRIPTION OF THE DRAWING

The FIGURE shows a flow diagram for a isobutane alkylation by catalytic distillation.

DESCRIPTION OF THE INVENTION

This invention relates to catalytic distillation techniques applied to isoparaffin alkylation with ofefins as well as to olefin oligomerization.

As mentioned, catalytic distillation involves a reaction zone containing catalyst fitted into a fractionation tower fitted with other conventional equipment. With reference to the drawing, olefin, isobutane and make-up $BF_3$ are fed to the reaction zone containing the catalyst bed. Water can be introduced into the catalyst bed as required. The distillation of reaction components occurs in the same temperature range as the reaction, that is, the alkylation or oligomerization. Here, alkylate product is withdrawn below the reaction bed while unreacted olefin and isobutane are withdrawn from above the reaction zone. As shown, both propane and butane can be separated in the distillation column with the $BF_3$ being recycled to the bed after being stripped from the propane. As shown, higher alkanes can be depropanized to further separate propane from butanes. The latter can be recycled to the column beneath the reaction zone or to a deisobutinizer to effect separation of normal butane and isobutane which is recycled beneath the catalyst bed to improve conversion.

As mentioned, catalytic distillation is suitable only for chemical reactions where the distillation of a reaction component occurs in the same temperature range as the reaction. Pressures to be utilized in the present process can extend over a considerably wide range and are conventional in the art.

The catalyst comprises a Lewis acid in combination with a non-zeolitic solid inorganic oxide, large pore crystalline molecular sieve and/or ion exchange resin. A Lewis acid is generally considered to be a molecule which is capable of combining with another molecule or ion by forming a covalent chemical bond with two electrons from the second molecule or ion, that is, the Lewis acid is an electron exceptor. Examples of Lewis acid include boron trifluoride ($BF_3$), boron trichloride ($BCl_3$), antimony pentafluoride ($SbF_5$) and aluminum chloride ($AlCl_3$). The present invention contemplates the use of all Lewis acids such as those set forth in *Friedel-Crafts And Related Reactions*, Interscience Publishers, chapters III and IV (1963), which is incorporated by reference.

The non-zeolitic solid inorganic oxide of this catalyst may be selected from among the diverse inorganic oxides including alumina, silica, boria, oxides of phosphorus, titanium dioxide, zirconium dioxide, chromia, zinc oxide, magnesia, calcium oxide, silica-alumina, silica-magnesia, silica-alumina-magnesia, silca-alumina-zirconia, chromia-alumina, alumina-boria, silica-zirconia, etc. and the various naturally occurring inorganic oxides of various states of purity such as bauxite, clay, diatomaeous earth etc. The preferred inorganic oxides are amorphous silicon dioxide and aluminum oxide.

The large pore crystalline molecular sieves which can be used in the present invention include those which have pores sufficiently large to physically absorb 2,2,4-trimethylpentane. Representative large pore crystalline molecular sieves include, for example the following zeolites: ZSM-3, ZSM-4, ZSM-12, ZSM-18, ZSM-20, zeolite Beta, zeolite L, mordenite, faujasite, zeolite Y, and the rare earth metal-containing forms of the above. For the purposes of this invention, zeolite Y includes zeolite Y in its as synthesized form, as well as its variant forms including framework dealuminated zeolite, e.g., ultrastable Y (USY) described in U.S. Pat. No. 3,293,192 and LZ-210 described in U.S. Pat. No. 4,503,023, hereby incorporated by reference.

The large pore zeolite selected for use in the improved alkylation process of this invention generally can possess an alpha value over a wide range of from less than 1 to over 1000. "Alpha value", or "alpha number", is a measure of zeolite acidic functionality and is more fully described together with details of its measurement in U.S. Pat. No. 4,016,218, *J. Catalysis*, 6, pp. 278-287 (1966) and *J. Catalysis*, 61, pp. 390-396 (1980). Zeolites of low acidity (alpha values of less than about 200) can be achieved by a variety of techniques including (a) synthesizing a zeolite with a high silica/alumina ratio, (b) steaming, (c) steaming followed by dealuminization and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures using elevated pressure, e.g., at from about 350° to about 700°F. with from about 10 to about 200 atmospheres. Specific details of several steaming procedures may be gained from the disclosures of U.S. Pat. Nos. 4,325,994; 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

Other large pore crystalline molecular sieves which can be used in the present invention include pillared silicates and/or clays; aluminophosphates, e.g., ALPO-5, VPI-5; silicoaluminophosphates, e.g., SAPO-5, SAPO-37, SAPO-31, SAPO-40, SAPO-41; and other metal aluminophosphates. These are variously described in U.S. Pat. Nos. 4,440,871; 4,554,143; 4,567,029; 4,666,875 and 4,742,033.

The particular class of macroreticular acid cation exchange resins used are characterized by substantial porosity, high surface area and a low surface acid concentration, generally less than about 0.5 milliequivalents of hydrogen ion per square meter surface area. The cation exchange resin can contain a small amount of water, generally between 0.5 and 20 percent by weight. The macroreticular resins utilized in the process of this invention are characterized by the presence of acid functional groups and a structure having a high degree of true porosity while possessing rigidity and being subject to minimum volume change when immersed or removed from solvents or solutions.

The macroreticular acid ion exchange resin used is typified by the presence of sulfonic acid groups, e.g., the sulfonated styrene-divinylbenzene copolymer exchange resins such as those commercially available as Amberlyst-15, Amberlyst XN-1005, Amberlyst XN-1010, Amberlyst XN-1011, Amberlyst XN-1008 and Amberlite 200. The properties of these resins along with Amberlite IR-120H, a typical microreticular resin, are shown below:

| Resin | Macrorecticular | | | | | | Microrecticular |
|---|---|---|---|---|---|---|---|
| | Amberlyst-15 | Amberlyst-XN-1005 | Amberlyst-XN-1010 | Amberlyst-XN-1013 | Amberlyst-XN-1008 | Amberlite-200 | Amberlite-IR-120H |
| Skeletal Structure | Styrene-DVB | " | " | " | " | " | " |
| Ionic Functionality | $RSO_3H$ | " | " | " | " | " | " |
| Hydrogen Ion Concentration meq/g dry (exchange Capacity) | 4.9 | 3.4 | 3.3 | 4.2 | 4.5 | 4.3 | 5.0 |
| Porosity % | 32 | 42 | 47 | 24 | — | — | 1.8 |
| Avg. Pore Diameter, A° | 200–600 | 80–90 | 40–50 | — | 400–800 | — | — |
| Cross-linkage | ~20 | — | — | — | — | ~20 | 8 |
| Surface Area, $m^{2/g\ dry}$ | 40–50 | 100–200 | 550–600 | 28 | 30–40 | 40–50 | <0.1 |
| Surface Acid Concentration meq $H^+/m^2$ S.A. | 0.102 | 0.031 | 0.006 | 0.150 | 0.129 | 0.096 | >50 |

ALKYLATION

Alkylation of isobutane with light olefins plays an important role in the manufacture of high octane gasoline blending stocks with alkylate typically comprising 10 to 15% of the gasoline pool. Alkylate is a particularly valuable portion of the gasoline pool as it has both high research and motor octane, contains no olefins or aromatics and little or no sulfur, demonstrates excellent stability and is clean burning.

A process has been developed for producing high octane gasoline utilizing catalytic distillation techniques. It includes a novel isoparaffin/olefin alkylation catalyst. The catalyst system includes a Lewis acid, such as $BF_3$, in combination with a non-zeolitic solid inorganic oxide, such as $SiO_2$, a large pore crystalline molecular sieve and/or ion exchange resin to promote paraffin/olefin alkylation. The Lewis acid is to be maintained at a level in excess of that required to saturate the non-zeolitic solid inorganic oxide, large pore crystalline molecular sieve, and/or ion exchange resin. The resulting alkylate is of a high quality based on both research and motor octane and is particularly suited for blending into a gasoline pool.

The operating temperature of the alkylation process can extend over a fairly broad range, for example, from about −50° C. to about 500° C. and is preferably within the range of from about −40° C. to about 250° C. The practical upper operating temperature will often be dictated by the need to avoid an undue occurrence of undesirable side reactions.

The pressures used in the present process can extend over a considerably wide range, for example, from subatmospheric to about 5000 psig, preferably to about 500 psig.

The amount of catalyst used in the present process can be varied over relatively wide limits. In general, the amount of catalyst, as measured by the weight hourly space velocity of the olefin, can range from about 0.01 to about 100. It will be realized by those skilled in the art that the amount of catalyst selected for a particular reaction will be determined by several variables including the reactants involved as well as the nature of the catalyst and the operating conditions used.

The particular operating conditions used in the present process will depend on the specific alkylation reaction being effected. Such conditions as temperature, pressure, space velocity and molar ratio of the reactants will have important effects on the overall process. Also, the operating conditions for the alkylation reaction according to this process may be varied so that the same may be conducted in gaseous phase, liquid phase or mixed liquid-vapor phase, depending upon product distribution, degree of alkylation, as well as the pressures and temperatures at which the alkylation is effected.

The isoparaffin reactant used in the present alkylation process is one possessing up to about 20 carbon atoms and preferably one having from about 4 to 8 carbon atoms as, for example, isobutane, 3-methylhexane, 2-methylbutane, 2,3-dimethylbutane and 2,4-dimethylhexane.

The olefin reactant used generally contains from 2 to about 12 carbon atoms. Representative examples are ethylene, propylene, butene-1, butene-2, isobutylene, and pentenes, etc. Particularly preferred are $C_3$ and $C_4$ olefins and mixtures thereof.

In general, the relative molar ratio between the isoparaffin reactant and the olefin alkylating agent can be from about 1:1 to about 50:1 and is preferably in the range of from about 5:1 to about 25:1.

Optionally, the alkylation process disclosed may be carried out with water added to the alkylation catalytic distillation column, that is, at a rate on average of from about 0.1 ppmw to about 1 wt. % based upon total hydrocarbon feed rate, preferably at a rate from about 0.1 to about 500 ppmw. The water can be supplied as such or be a feed material which provides water under the alkylation condition selected. Suitable water-forming materials which can be introduced into the distillation column without interfering with the desired alkylation include monohydric and dihydric alcohols which yield water upon undergoing dehydration. Of this group, particular preference is accorded the aliphatic alcohols, especially those containing 1 to 6 carbon atoms, for example, methanol, ethanol, isopropanol, t-butyl alcohol and isopentyl alcohol. The water and/or water-producing material can be added directly to the distillation column, that is, as part of the feed and/or it can be incorporated in the catalyst, either by direct contact or by exposing the catalyst to an atmosphere of water and/or water-forming material. The amount of water preintroduced into the catalyst ranges from about 0.5 to about 25 percent by weight of the catalyst, preferably from about 1 to about 10 percent.

Experimentation

The following examples will service to illustrate this alkylation process of the invention without limiting it.

EXAMPLE 1

The specific alkylation operating (non-catalytic distillation) conditions used in this example are set forth in Table 1.

TABLE 1

BF$_3$ PROMOTED ALKYLATION OPERATING CONDITIONS

| | |
|---|---|
| Temperature, °C. | 20 |
| Pressure, psig | 150 |
| Stirring Rate, rpm | 1900 |
| BF$_3$ Feed Rate, wt % of HC Feed | 3.0 |
| HC Feed, i-C$_4$/olefin ratio | 10/1 |
| Olefin WHSV, hr$^{-1}$ | 1.2 |

MIXED C$_3$/C$_4$ OLEFIN DISTRIBUTION, WT %

| | |
|---|---|
| Propylene | 42.5 |
| 1-Butene | 13.7 |
| Cis + Trans-2-Butene | 28.2 |
| Isobutylene | 15.6 |

The solid inorganic oxide used in this example is a commercially available amorphous SiO$_2$ (0.5 wt. % Al$_2$O$_3$). The as-received material is calcined at 1000° F. and sized to 100/200 mesh before use in the alkylation reactor.

In a standard start-up procedure, 10 grams of catalyst is placed in the 300 ml autoclave reactor, and about 300 ml of isobutane is charged to fill the reactor. The resulting mixture is cooled to the desired temperature with constant stirring at 1900 rpm and BF$_3$ gas is introduced into the reactor. After BF$_3$ breakthrough is observed, the BF$_3$ flow rate is then reduced to a level equivalent to 3 wt % of total hydrocarbon feed rate. At this point, the isobutane/olefin mixture is continuously fed into the reactor to initiate the catalytic alkylation. The feed is a simulated commercial feed (approximately 10/1 i-C$_4$/mixed olefins) approximating the C$_3$=/C$_4$= fraction produced from an FCC. The operating conditions as set forth in Table 1 are 150 psig, 20° C., 1900 rpm, 1.2 WHSV based on olefin and 3.0 wt % BF$_3$ based on total hydrocarbon feed rate. The product is continuously withdrawn from the reactor and is weathered to atmospheric pressure via a back pressure regulator and then sent to a receiver which is kept at 0° C. Periodically, the product is drained from the receiver and weathered at room temperature prior to analysis.

An on-line gas chromatograph coupled with an automatic sampling device is used to monitor the course of the alkylation reaction. All reported octane numbers are measured. The isobutane (C.P. grade), isobutane/mixed C$_3$+C$_4$ olefins and BF$_3$ (C.P. grade) are used without further purification. Water was added intermittently throughout the run at an average rate of about 100 ppmw based upon total hydrocarbon feed rate.

The resulting yield and octane data for the BF$_3$/SiO$_2$ catalyst system is summarized in Table 2.

TABLE 2

Alkylation Of Isobutane by C$_3$/C$_4$ Olefins Using BF$_3$ Promoted Silica Catalyst

| | |
|---|---|
| Yield, g C$_5$+/g Olefin Converted | 2.1 |
| Yields in C$_5$+, Wt % | |
| C$_5$ | 2.7 |
| C$_6$ | 2.3 |
| C$_7$ | 27.1 |
| C$_8$ | 61.4 |
| C$_9$+ | 6.4 |
| RON + 0 | 93 |
| MON + 0 | 90 |

EXAMPLE 2

Alkylation of Isobutane by C$_3$/C$_4$ Olefins Using Catalytic Distillation

Example 1 is repeated. A flow diagram of this experimental technique is illustrated in FIG. 1. The catalytic distillation takes place in a vessel similar to a distillation tower with solid catalyst in some of the trays. Olefins are introduced into the catalyst bed along with isobutane and BF$_3$. The alkylate product is separated from lighter reactants and is withdrawn from the column bottom. Heat of reaction drives unreacted isobutane (and BF$_3$) up the column for recovery and recycle.

The requirement that the reactants boil in the range of the reaction temperature is accomplished by adjusting reactor pressure. This may range from sub- to super-atmospheric conditions depending on the particular reactants involved.

OLIGOMERIZATION

Another embodiment of this invention relates to oligomerization utilizing catalytic distillation techniques. The oligomerization technique is described in U.S. Pat. No. 4,308,414, as well as in N. Morganson et al, *Fixed-Bed Catalytic Process To Produce Synthetic Lubricants From Decene*-1, Industrial Engineering Product Research Development, Vol. 22, No. 4, p. 675-670 (1983), hereby incorporated by reference.

The subject process is directed to an alpha-olefin which is oligomerized in the presence of a catalyst comprising boron trifluoride, a minute amount of water in a particular adsorbent material such as silica to a product predominating in those oligomer fractions having viscosities within the lubricating oil range such as the trimer and tetramer of 1-decene. The catalyst has been described above in the earlier embodiment involving alkylation and will not be repeated here for the sake of brevity.

1-decene is the most preferred alpha-olefin for preparing synthetic lubricants and related functional fluids. This is the preferred alpha-olefin for this oligomerization. However, 1-olefins having from 3 to 20 carbon atoms and preferably 8 to 12 carbon atoms or various combinations of these alpha-olefins can also be used. Straight chain olefins are preferred.

The solid adsorbent material of the present invention may be either inorganic or organic, should have a surface area of at least about 0.1 m$^2$ per gram and must be insoluble in the reaction liquid. The inorganic oxide of this catalyst may be selected from among the diverse inorganic oxides including alumina, silica, boria, oxides or phosphorus, titanium dioxide, zirconium dioxide, chromia, zinc oxide, magnesia, calcium oxide, silica-alumina, silica-magnesia, silica-alumina-magnesia, silica-alumina-zirconia, chromia-alumina, alumina-boria, silica-zirconia, etc. and the various naturally occurring inorganic oxides of various states of purity such as bauxite, clay, diatomaeous earth etc.

It is desirable that the maximum reaction temperature be about 150° C., preferably no higher than about 100° C. and most preferably no higher than about 50°C.

Regarding particle size of the catalyst, the smaller the particle size the greater the activity at constant catalyst volume. However, a catalyst bed formed from too finely sized particles tends to restrict the flow of the reaction streams. For these reasons, the particle size of the catalyst is preferably at least about 100 mesh (0.15 mm) in particle size and most preferably at least about 50 mesh (0.3 mm). The maximum particle size is preferably about 3 mesh (6.7 mm) and most preferably about 10 mesh (2.0 mm). However, products can be prepared with solid adsorbent outside these limits of particle size.

Regarding a feed rate for the boron trifluoride, in general, it will be at least about 0.1 wt. % of the 1-olefin. Even though the oligomerization reaction can be carried out at atmospheric pressure when using pure boron trifluoride, it is desirable to maintain a partial pressure of boron trifluoride in the reactor of at least about 10 psig (0.17 MPa) for suitable catalyst activity and preferably at least about 50 psig (0.44 MPa) for superior catalyst activity. Partial pressures of boron trifluoride as high as about 500 psig (3.55 MPa) and higher can be utilized but it is preferred that an operating partial pressure of about 250 psig (1.83 MPa) not be exceeded.

The oligomerization reaction in a fixed bed can be conveniently carried out within the broad range of liquid hourly space velocities, that is, the volume of the liquid feed per volume of catalyst per hour of about between 0.1 and about 50 hours$^{-1}$; but preferably the reaction is carried out within the range of about 0.5 and about 10 hours$^{-1}$.

The following examples will serve to illustrate this oligomerization process of the invention within limiting it.

EXAMPLE 3

A reactor used containing 60 cc of a fresh batch of 40/50 mesh (0.3 to 0.42 mm) silica which had been pretreated with boron trifluoride under pressure. 1-decene containing 42 ppm water was fed to the reactor at a rate of 300 cc per hour which is a liquid hourly space velocity of 5.0 hour$^{-1}$. Boron trifluoride gas was fed to the 1-decene immediately prior to the reactor at a rate of 38.8 cc per minute, which was 3.14 wt. % boron trifluoride based on the 1-decene . The reactor outlet was operated at 150 psig (1.14 MPa). The maximum steady state temperature after 43 hours was 21° C. The percent conversion was 90.6%. See U.S. Pat. No. 4,308,414.

EXAMPLE 4

Example 3 is repeated, except that a catalytic distillation technique was utilized to effect the reaction. The catalytic distillation takes place in a vessel similar to a distillation tower with solid catalyst in some of the trays as mentioned in Example 2. Reactants are introduced into the catalyst bed or reaction area. Product is withdrawn from beneath the reaction area, while unreacted reactants are withdrawn above the reaction zone.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A continuous process comprising:
    (a) feeding (1) an isoparaffin containing from 4 to 20 carbon atoms and (2) an olefin containing from 2 to 12 carbons atoms to a distillation column reactor into a feed zone,
    (b) concurrently in the distillation column reactor; contacting the isoparaffin and olefin with a composite catalyst consisting essentially of a Lewis acid in combination with a non-zeolitic solid inorganic oxide in a distillation reaction zone thereby catalytically reacting the isoparaffin with the olefin to from alkylate,
    (c) withdrawing the alkylate from the distillation column reactor below the feed zone, and
    (d) withdrawing the isobutane from the distillation column reactor above the feed zone.

2. The process according to claim 1, wherein the isoparaffin contains from 4 to 6 carbon atoms and the olefin contains from 2 to 6 carbon atoms.

3. The process according to claim 1, wherein the Lewis acid is $BF_3$, $BCl_3$, $SbF_5$, $AlCl_3$ and admixtures thereof.

4. The process according to claim 1, wherein the Lewis acid is $BF_3$.

5. The process according to claim 1, wherein the non-zeolitic inorganic oxide is $SiO_2$, $Al_2O_3$, $ZrO_2$ or admixtures thereof.

6. The process according to claim 1, wherein the non-zeolitic inorganic oxide is $SiO_2$ or $Al_2O_3$.

7. The process according to claim 1, wherein the catalyst is $BF_3/SiO_2$.

8. The process according to claim 1, wherein the reaction is conducted under sufficient pressure to maintain at least one of the reactants in the liquid phase.

9. The process according to claim 1, wherein the molar ratio of the isoparaffin to the olefin is from 1:1 to about to 50:1.

10. The process according to claim 9, wherein the molar ratio of the isoparaffin to the olefin is from 5:1 to about 25:1.

11. The process according to claim 1, wherein the isoparaffin is isobutane and the olefin is propylene or butene.

12. The process according to claim 1, wherein the contacting the isoparaffin and olefin with a composite catalyst occurs in the presence of water.

13. The process according to claim 12, wherein the water or water-producing material is preintroduced into the catalyst.

14. The process according to claim 12, wherein the water or water producing material is cofed with the reactants.

15. The process according to claim 13, wherein the amount of water preintroduced into the catalyst ranges from about 0.5 to about 25 percent by weight of the catalyst.

16. The process according to claim 15, wherein the amount of water preintroduced into the catalyst ranges from about 1.0 to about 10 percent by weight of the catalyst.

17. The process according to claim 14, wherein the amount of water ranges from about 0.1 ppmw to about 1 weight percent based upon total hydrocarbon feed rate.

18. The process according to claim 17, wherein the amount of water ranges from about 0.1 ppmw to about 500 ppmw based upon total hydrocarbon feed rate.

19. The process according to claim 12, wherein water is added intermittently to the reaction.

20. The process according to claim 1, wherein reaction temperature is from about −40° C. to about 250° C.

21. The process according to claim 1, wherein the weight hourly space velocity of the olefin is from about 0.01 to about 100.

22. The process according to claim 1, wherein the Lewis acid is present in an amount in excess of that required to saturate the solid inorganic oxide.

23. The process according to claim 1, wherein the Lewis acid is withdrawn from the distillation column reactor above the feed zone.

24. The process according to claim 1, wherein the Lewis acid is recycled.

25. A continuous oligomerization process comprising:

(a) feeding alpha-olefins having from 3 to 20 carbon atoms to a distillation column reactor into a feed zone, (b) concurrently in the distillation column reactor: contacting the alpha-olefins with a composite catalyst consisting essentially of a Lewis acid with a non-zeolite solid inorganic oxide in a distillation reaction zone thereby catalytically reacting the alpha-olefins to form oligomer, (c) withdrawing the oligomer from the distillation column reactor below the feed zone, and (d) withdrawing unreacted alpha-olefins from the distillation column reactor below the feed zone.

26. The oligomerization process according to claim 25, wherein the contacting of alpha-olefins with composite catalyst occurs in the presence of water.

* * * * *